(12) United States Patent
Leonardi Kader (10) Patent No.: US 8,956,345 B2
(45) Date of Patent: Feb. 17, 2015

(54) METHOD AND APPLIANCE FOR COSMETIC SKINCARE

(76) Inventor: Simone Nadia Leonardi Kader, Nice (FR)

( * ) Notice: Subject to any disclaimer, the term of this patent is extended or adjusted under 35 U.S.C. 154(b) by 437 days.

(21) Appl. No.: 13/262,508

(22) PCT Filed: Mar. 31, 2010

(86) PCT No.: PCT/FR2010/000274
§ 371 (c)(1),
(2), (4) Date: Nov. 22, 2011

(87) PCT Pub. No.: WO2010/112708
PCT Pub. Date: Oct. 7, 2010

(65) Prior Publication Data
US 2012/0065575 A1    Mar. 15, 2012

(30) Foreign Application Priority Data

Mar. 31, 2009 (FR) ...................... 09 01584

(51) Int. Cl.
*A61B 18/18* (2006.01)
*A61N 5/06* (2006.01)
*A61N 1/32* (2006.01)

(52) U.S. Cl.
CPC .............. *A61N 5/0616* (2013.01); *A61N 1/325* (2013.01); *A61N 1/327* (2013.01); *A61N 2005/0663* (2013.01)
USPC ......... 606/9; 606/32; 606/42; 607/88; 607/98

(58) Field of Classification Search
None
See application file for complete search history.

(56) References Cited

U.S. PATENT DOCUMENTS

| 2005/0148996 | A1* | 7/2005 | Sun et al. ....................... 604/501 |
| 2005/0177207 | A1 | 8/2005 | Berg et al. |
| 2006/0253078 | A1 | 11/2006 | Wu et al. |
| 2007/0060862 | A1 | 3/2007 | Sun et al. |
| 2007/0198004 | A1* | 8/2007 | Altshuler et al. ................. 606/9 |
| 2010/0274329 | A1* | 10/2010 | Bradley et al. .................. 607/90 |

FOREIGN PATENT DOCUMENTS

| CA | 2 363 383 A1 | 5/2003 |
| KR | 2003-0016533 A | 3/2003 |

* cited by examiner

*Primary Examiner* — Lynsey Crandall
(74) *Attorney, Agent, or Firm* — IM IP Law PLLC; C. Andrew Im (57) ABSTRACT

The invention relates to the field of cosmetology. The invention relates to cosmetic or aesthetic skin treatment using an appliance, in particular for dermatological care, which combines applying pulsed electrical currents to the skin for treating the skin by electroporation in a first step, constant currents for electrophoretically treating the skin in a second step, with the simultaneous exposure of the skin under treatment to chromotherapeutic light emissions in which the color changes from one step to the next. The color red is preferred for electroporation; orange is preferred during the electrophoretic treatment. The appliance is programmed for automatic is programmed for automatic operation. The method advantageously comprises a third chromotheraphy step under blue light combined with the application of an electrophoretic current.

18 Claims, 7 Drawing Sheets

METHOD AND APPLIANCE FOR COSMETIC SKINCARE

CROSS-REFERENCE TO RELATED APPLICATION

This application is a National Stage entry of International Application No. PCT/FR2010/000274, filed Mar. 31, 2010, which claims priority to French Patent Application No. 0901584, filed Mar. 31, 2009, the disclosure of the prior applications are incorporated in their entirety by reference.

The present invention relates to an appliance for treating the skin, especially for dermatological treatment, particularly for therapeutic or esthetic purposes, which appliance is more particularly though not limitingly intended for cosmetological use, for example to treat pigmentation marks that make the skin less attractive, to reduce certain visible effects of aging, especially to rejuvenate the skin or to increase the firmness of the skin.

The invention also relates to a cosmetological treatment method, especially a beauty treatment, which is implemented using the appliance in question. This method is in particular used to subject the skin to physical actions that complement active ingredients known for their chemical, or indeed biochemical, activity, such as those commonly applied to the skin in the form of cosmetic creams, gels, solutions, or in any form suitable for local dermatological application to the skin. This however does not exclude also using the appliance according to the invention to increase the effectiveness of other products that are applied to the skin, including use in treatments employing medicinal active ingredients, especially to increase the penetration of active pharmacological compounds into the epidermis.

Cutaneous pigmentation marks, such as chloasma, melasma and age spots, may appear on the face, neck, chest, forearms, the backs of the hands, and in regions of bodily friction. They are not solely the concern of the elderly as they are also a problem for relatively young people. Generally, apart from natural aging of the skin, they may be caused by factors as diverse as the sun, pregnancy, certain medical treatments, contraceptives, to mention just a few examples.

To reduce the visibility of these marks, or even to make them disappear, techniques exist that consist in removing the horny layer of the skin responsible for the presence of the marks. Either the top part of the epidermis is removed in the location of the mark by dermabrasion or peeling, or it is sought to burn the faulty pigments by exposure to radiation, such as a laser beam, which burns the skin in the location of the marks. These treatments, which are aggressive to the epidermis, furthermore have the drawback of not being suited to all skin types. For example, it is in particular inadvisable to expose dark skin to a laser beam (in particular, a hyperpigmentation reaction has been observed in certain cases). It follows that implementation of these techniques requires a specialist capable of defining specific case-by-case adjustments to be made depending on the skin type of the patient (especially between light skin and dark skin), depending on the location of the marks to be treated, their origin and their age, and also depending on the general condition of the skin at the time of treatment.

Cosmetology techniques, whether or not employing a chemical action, and more specifically those that make use of electrical currents, are therefore preferred to the above treatments that are too physically aggressive. Techniques that use pulsed currents to induce electroporation effects and others that use DC currents of constant polarity under conditions that specifically induce electrophoresis effects in the epidermis are thus known.

By way of example, document US 2007/060862 describes an appliance for treating the skin, comprising a membrane and means for producing a pulsed or DC electrical current, and light-emission means, especially LEDs. The LEDs modulate the current flowing through the membrane so as to form a pulsed DC current, so as to improve drug delivery and stimulate biological response. On this occasion, the appliance may comprise two LEDs emitting at wavelengths of 400-500 nm and 700-1000 nm. This appliance is of limited effectiveness.

Document KR 2003 0 016 533 describes a heat-therapy appliance of compact size using infrared radiation. This appliance comprises a means for emitting infrared radiation, means for emitting heat and means for making a current flow. Here again, this appliance is of limited effectiveness.

Document US 2006/253078 describes an appliance for treating the skin, in particular comprising a membrane intended to make contact with the skin, a power supply, two conductive electrodes and a reservoir. The power supply is in electrical communication with the first electrode and the second electrode, the electrodes being placed so as to be in ionic communication with a carrier present in the reservoir. The appliance may be designed so as to comprise an LED and the light emitted may be in communication with the membrane. The power supply may supply DC current or pulsed current. The appliance may, in one particular embodiment, comprise two LEDs emitting at wavelengths of 400-500 nm and 700-1000 nm. The effectiveness of this appliance could be improved.

Finally, document US 2005/177207 describes a method for inhibiting cell growth or for enhancing cell death by electroporation of a photosensitive agent in a cell. The method consists more particularly in administering a photosensitive agent for treatment of cell proliferative disorders via application of an electrical pulse to the cell, the pulse being of sufficient height and of sufficient duration for the cell to be electroporated with the photosensitive agent, and in applying light of a wavelength permitting activation of the agent and treatment of the proliferative disorder. The electrical pulse may be a suitable pulsed electric field via an electroporation appliance. The light may be applied before, during or after the electroporation. The wavelength depends on the energy required to activate the photosensitive agent: it may be 560 nm.

These treatments are in general implemented as a complement to the application of active ingredients mixed with an appropriate vehicle in a composition for local application: cream, lotion, etc.

To provide optimal effectiveness and minimal aggression to the skin, the invention involves subjecting the skin to a cycle of a number of different treatments, each of which has a specific effect on the skin, under conditions in which the respective effects of the treatments are mutually maximized. Advantageously, together these treatment cycles have a synergistic action. The method according to the invention and the appliance designed to implement it have the particularity of applying term, in a predefined succession, predefined sequences of DC currents and pulsed currents to the skin in combination with sequences of illumination of the region to be treated by light of different colors.

More particularly, the subject of the invention is a method essentially consisting in subjecting the skin to a cycle of successive sequences comprising at least a first sequence for treating the skin by applying a pulsed electroporation current in combination with simultaneous exposure of the skin under treatment to light of warmer color, and a second sequence for treating the skin by applying a DC electrophoresis current in combination with simultaneous exposure of the skin under treatment to light of colder color.

The term "warmer color" is, in the context of the present invention, understood to mean a color comprising wavelengths lying between 692 nm and 800 nm, the lower limit of 692 nm not being included in this range. For example, the wavelengths may lie between 764 nm and 780 nm. It may for example be a color chosen from red-orange, red and red-violet. Advantageously, application of this color may be able to maximize the electroporation effect. Application of this color may increase the effect of treating the skin by electroporation alone. Advantageously, the electroporation effect may be at least doubled compared with the use of electroporation alone. The application of this color may have a synergistic effect with the electroporation. The maximizing of the electroporation effect may be observed or measured by any means known to a person skilled in the art, for example by visual inspection or by digital photography, this list not being exhaustive. Advantageously, the light intensity may make it possible to maximize the effects of applying the color. The light intensity associated with this color may lie between 70 and 150 candelas, for example between 120 and 150 candelas, or indeed between 130 and 150 candelas.

The term "colder color" is, in the context of the present invention, understood to mean a color comprising wavelengths lying between 560 nm and 692 nm, the lower limit of 560 nm not being included in this range. For example, the wavelengths may lie between 580 nm and 692 nm, 692 nm being included in this range. It may for example be a color chosen from yellow, yellow-orange and orange. Application of this color may increase the effect of treating the skin by electrophoresis alone. Advantageously, the electroporation effect may be at least doubled compared with use of electrophoresis alone. The application of this color may have a synergistic effect with the electrophoresis. The maximizing of the electrophoresis effect may be observed or measured by any means known to a person skilled in the art, for example by visual inspection or by digital photography, this list not being exhaustive. Advantageously, the light intensity may make it possible to maximize the effects of applying the color. Advantageously, the light intensity associated with this color may lie between 30 and 69 candelas, for example between 40 and 60 candelas.

Preferably, the first sequence, called the electroporation sequence, and the second sequence, called the electrophoresis sequence, form two steps that are performed in succession in this order during the implementation of the method of the invention. As for the colors of light to be used, red light is preferably employed in the electroporation step and orange light is preferably employed in the electrophoresis step. It will be noted that, in both cases, the light used remains in the warm color range of the visible spectrum, i.e. colors corresponding to relatively long wavelengths.

Thus, the invention in particular relates to a method for the aesthetic treatment of, or for the dermatological treatment of, the skin, in which the skin is subjected to a cycle of successive sequences comprising, in this order, at least a first sequence for treating the skin, called an electroporation sequence, comprising applying a pulsed electroporation current to the skin in combination with simultaneous exposure of the skin under treatment to light having wavelengths lying between 692 nm and 800 nm, and a second sequence for treating the skin, called an electrophoresis sequence, comprising applying a DC electrophoresis current in combination with simultaneous exposure of the skin under treatment to light of wavelengths shorter than those applied in the first treatment sequence, for example ranging from 560 nm to 692 nm.

The expression "aesthetic treatment" is, in the context of the present invention, understood to mean use of any non-therapeutic treatment to improve the appearance of healthy skin. It may in particular be a cosmetic, cosmetological, or cosmeceutical treatment. The method may for example enable treatment of benign cutaneous pigmentation marks, not associated with a pathology such as chloasma, melasma, age spots, this list not being exhaustive. Advantageously, the method may make it possible to reduce the visibility of these marks. It may involve reducing the size of the marks. Advantageously, the size of the marks may be reduced by a third or else halved, or indeed reduced by three-quarters. A person skilled in the art may observe the reduction in the size of the mark by any known method, for example by visual inspection or by digital photography, this list not being exhaustive. Advantageously, the treatment may make it possible to bring the color of the pigmentation mark closer to that of the healthy skin, for example by making the mark lighter. For example, the mark may be made at least two times, or even three or four times lighter. A person skilled in the art may observe the color change of the mark using any known method, for example by visual inspection or by digital photography, this list not being exhaustive. Advantageously, the aesthetic treatment of the skin may have the aim of overall rejuvenation of the skin of the face, hands and body; the specific treatment of wrinkles; firming of slackening; treatment of cellulite; treatment of stretch marks. The skin treated may be light skin, dark skin and black skin.

The expression "dermatological treatment" is understood to mean any treatment of a skin disease, for example acne.

The expression "patient" is, in the context of the present invention, understood to mean any individual to which the method or appliance is applied, whether this application is for a aesthetic or for a therapeutic treatment.

By using light lying within the visible spectrum, such that it may be defined by its color, it is possible to consider that the invention applies chromotherapy (also called chromatherapy) effects to the skin, which it proposes to combine in a specific way with treatments involving application of electrical currents, by varying the color from one step to another.

In preferred implementations of the invention, the same treatment cycle comprises a third sequence consisting of a treatment for regenerating the skin via exposure to light having a cold color.

The expression "cold color" is, in the context of the present invention, understood to mean a color comprising wavelengths lying between 330 nm and 560 nm, 560 nm being included in this range. It may for example be a color chosen from blue-violet, blue, blue-green, green and yellow-green. Advantageously, this color may be able to improve regeneration of cells in the epidermis, for example by rehydrating the cells of the epidermis. Advantageously, application of this color may provide the skin with a smoother and/or silkier appearance. Advantageously, application of this color may make it possible to brighten the complexion. A person skilled in the art will be able to observe or measure one or more of these improvements using any known method, for example by visual inspection or by digital photography, this list not being exhaustive. Advantageously, the light intensity may make it possible to maximize the effects of applying the color. Advantageously, the light intensity associated with this color may lie between 2 and 29 candelas, for example between 10 and 20 candelas.

This color typically lies within the short-wavelength range, particularly including blue light.

In accordance with secondary features specific to the invention, the cycle for treating the skin, in its third sequence, therefore consists essentially of a treatment for regenerating the skin via chromotherapy, under exposure to light of cold color, such as blue light. In most applications, it will be advantageous to combine this chromotherapy treatment with an electrophoresis treatment. Advantageously, this combination may make it possible to maximize the regeneration effect on the skin. During the third step of the method, it is therefore in general advantageous to apply a current that has an electrophoretic action, such as that of the second step.

This is true especially when the current is chosen to have a suitable polarity so as to contribute, via electrophoresis, to the penetration through the epidermis of active ingredients contained in a composition applied locally on the skin. A person skilled in the art will know how to choose the polarity to be used in general depending on the properties of the vehicle present in said composition as a mixture with the active ingredients. This is because, and as will have already been understood from the description of the prior art, the preferred conditions for applying the method according to the invention comprise, before the cycle of application of current and simultaneous exposure to colored light, in its two or three sequences, deposition on the skin of a cosmetic composition for local application to the skin. In the context of the invention, such a composition preferably takes the form of a lotion, because the fluidity of this presentation form enhances the effectiveness of treatments that apply a flow of electrical current, in comparison with the use of creams or gels.

Advantageously, an active ingredient of the cosmetic composition deposited on the skin may have an anti-aging effect, a hydrating effect, an effect that reduces the appearance of cellulite or a depigmentation effect.

For example, an active ingredient may be chosen from mandelic acid, salicylic acid, retinoic acid, retinol, forskolin, carnitine, glycerol, sorbitol, hyaluronic acid, silicone, paraffin, this list not being exhaustive.

An appliance according to the invention, such as designed to allow the above method to be implemented, comprises means that are conventional per se, at least in their general definition. This applies mainly, on the one hand, to the means for producing an electrical current of predefined polarity between one electrode to be brought into contact with the skin of the patient in the region to be treated and an opposed electrode to be brought to a reference potential, and which is generally hand-held by the patient for this purpose. It also applies, on the other hand, to the means for producing colored light that is directed toward the skin in the region to be treated, in general electric lamps, and more particularly light-emitting diodes.

The means for producing colored light may be those that are commercially available, such as for example colored light bulbs.

The specific means of the invention in the appliance in question relate, on the one hand, to the automatic control of the electrical means and the illumination means, and the automatic control of the timing of the successive sequences of the treatment cycle. They also relate, on the other hand, to the mechanical mounting of the various functional elements that act on the skin in an insulating-case applicator head that the person carrying out the treatment, i.e. a medic or beauty therapist, holds in their hand so as to apply it to the skin of the patient.

The automatic control of the electrical means and the illumination means may be carried out using any commercially available means.

In its entirety, the appliance according to the invention comprises, in this head, an electrode to be applied to the region of skin to be treated and an assembly of light-emitting diodes as illumination means placed near this electrode so as to illuminate the region of skin to which the electrode is applied, and it also comprises, in a separate casing, an electronic unit that groups together the various electrical means for generating current of predefined polarity, alternately in pulsed mode or in nonpulsed mode (more advantageously still DC current of the same polarity, in contrast to an AC current), and programmed variable-parameter means for controlling the operating conditions of the appliance.

More precisely, the appliance according to the invention, in its preferred embodiments, includes means comprising microprocessors that are programmed for automatically controlling the distribution of electrical current on the one hand to said electrode and on the other hand to the various diodes, according to an operating cycle comprising the two or three sequences of the method defined above.

In other words, the appliance according to the invention comprises automatic control means for switching the electrical current produced between a pulsed electrode-supply current and a nonpulsed electrode-supply current of the same polarity and for controlling in synchronism the turn-on of diodes emitting light of various colors each of which is associated with a current type having predefined characteristics. It will be noted here that although switching between the illumination colors is synchronized with the switching of the current type applied to the electrode, this does not necessarily mean that the two operations occur strictly at the same instant, since it is equally possible for an electrophoretic current in particular to be still applied when the illumination color has already changed from orange to blue in the last step of the operating cycle.

Most frequently, the appliance will provide a plurality of predefined treatment programs for the practitioner using the appliance to choose from. The parameters of which the values will possibly vary from one program to another are principally the respective durations of each of the treatment steps. Their values will be set in each program with regard to the phototype, the various skin types among the commonest in the location of the skin to be treated, and the cosmetic modification to be provided.

For example, the duration of the method may be between 20 and 30 minutes.

For example, the first sequence for treating the skin may have a duration that makes it possible to open the pores of the skin. Advantageously, this duration may be between 5 and 30 minutes.

The second step for treating the skin may have a duration that makes it possible for the active substances present on the skin to migrate. Advantageously, this duration may be between 1 minute and 10 minutes.

The third step for treating the skin may have a duration may have a duration that makes it possible for the skin to regenerate. Advantageously, this duration may be between 30 seconds and 10 minutes.

The predefined programs may also be parameterized so that each may be used in association with a lotion composition chosen from the various lotions available to the practitioner. One of the parameters set in each program is then advantageously the polarity of the current, in addition to the duration of the various steps. As for the magnitude of the current, this may preferably be adjusted by the practitioner at any moment, depending on the sensations experienced by the patient.

In preferred (but nonlimiting) implementations of the invention, the quantities that can thus be parameterized are, on the one hand, the respective durations of the various operating sequences and, on the other hand, the magnitude, polarity and pulse-frequency characteristics of the electrical current applied in each of the sequences. In general, no provision is made to vary the parameters for concomitant illumination conditions, since the colors red, orange and blue are available by construction, except if necessary as regards the light intensity of each color emitted. The current supplied to the light sources allows their intensity to be easily varied, and thus the values set may be different from one color to another and/or in one or other of a plurality of programs prerecorded in the electronic unit for controlling the appliance.

The polarity of the current may be positive or negative, depending on the polarity of the composition applied to the skin.

The magnitude of the current may be between 1 mA and 10 mA, for example between 2 mA and 8 mA, or else between 3 mA and 5 mA for all the sequences variable between 0 and 10 mA.

The pulse frequency during the electroporation sequence may be between 100 μs and 300 μs.

From the point of view of its mechanical construction, the appliance according to the invention is mainly characterized, in its preferred embodiments, by the fact that it comprises, in the applicator head for application to the skin, light-emitting diodes that illuminate the skin with colored light and which are distributed in a ring around an electrode that makes axial contact with the skin to be treated. In general it is most advantageous to provide a plurality of diodes for each color, which diodes are alternated, in interleaved succession following rules of rotational symmetry, around the electrode. This makes it possible to supply a uniform illumination in the immediate vicinity of the end of the electrode brought into electrical contact with the skin, whatever color is being emitted.

It will be noted that, according to one preferred embodiment of the invention, only the electrode of the applicator head is intended to make contact with the skin to be treated, the diodes never making contact with the skin and being protected therefrom by an insulating window-pane made of a material transparent to visible radiation, in general mineral or organic glass. Even more advantageously, this window-pane is translucent.

According to another feature of the invention, in one advantageous variant embodiment of the appliance, the applicator head is shaped so as to house, in its end intended to be placed in contact with the skin to be treated, a quartz crystal, or another type of mineral having a lithotherapy effect when it is brought into contact with the skin at the same time as the electrode. This element is advantageously placed around the electrode in front of the light-emitting diodes in the applicator head for application to the skin.

Advantageously, the mineral may increase or amplify the treatment effect. The mineral may for example enhance migration of the active substances present on the skin, and/or relax the skin. Although this mechanism should not be considered binding to the Applicant, it is possible for the amplification to be a result of the specific piezoelectric properties of the mineral. The piezoelectricity of the quartz crystal may for example increase blood flow to the skin and therefore improve migration of the active substance present on the skin.

As the presence of a lithotherapy quartz crystal makes the applicator head relatively bulky at its end part to be applied to the skin, it is in general desirable to provide a given appliance with an interchangeable head that is not equipped with such a quartz crystal, which is then used to treat regions of skin that are hard to reach, around the eyelids for example.

Whatever the embodiment used, a set of seals, especially placed between the electrode and the translucent windowpane or the lithotherapy-effect quartz crystal, seal against active cosmetic substances optionally deposited on the skin before the appliance according to the invention is used.

Other features and advantages of the invention will become clear from details of a practical embodiment of a particular appliance according to the invention, described below with reference to the figures that illustrate its description, in which figures.

The appliance according to the invention is described here in the context of its use to promote the action of active ingredients contained as a mixture with an appropriate vehicle in a composition in the form of a lotion for cosmetic treatment, which is deposited beforehand on the region of skin to be treated.

The essential elements of the appliance are distributed between a housing A for electrics and electronics and a treatment head 7 shaped to be held in the practitioner's hand. The treatment head has an end part to be brought into contact with the skin and moved over the surface of the skin to be treated, in the location of pigmentation marks to be treated. This is where the electrode 9 is located axially, the end of which electrode makes contact with the skin, and also where the diodes 4 emitting colored light are located. The electrical circuit of the electrode is completed, through the patient's body, on an opposed reference electrode, drawn as element 21 in FIG. 1, which is shaped to be held by the patient in electrical contact with the hand.

Figure 1:
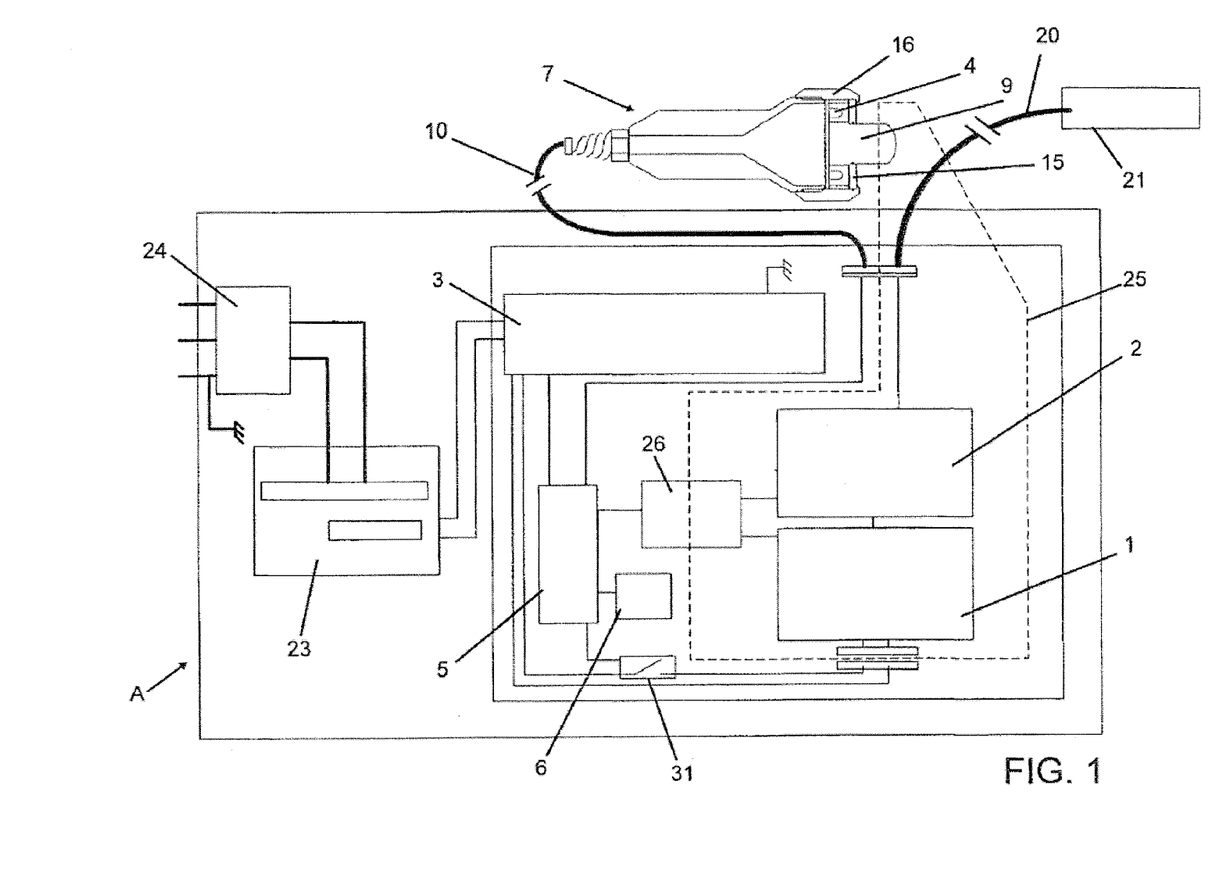
FIG. 1 is a schematic view of the appliance according to the invention showing more specifically the form of the electrical assembly comprising its electronic control unit.

The associated housing A contains an electrical power supply unit 3 to be plugged into an external supply via a filter 24 and a transformer 23. The unit 3 supplies the necessary power to a DC current generator 1 and to a pulse generator 2. The current produced is in both cases under low voltage, a potential difference of 12 volts typically being applied between the treatment electrode 9 and the reference electrode 21, via electrical cables 10 and 20 respectively.

The magnitude of the current delivered to the treatment electrode can be varied within a preset range of values, typically up to a maximum of 10 milliamps. The magnitude can be varied throughout each operating cycle of the appliance via action on a button that is accessible to the user on the side of the housing. For an optimal electroporation effect, as opposed to the electrophoresis effect sought during application of the nonpulsed current, the pulsed current generator delivers pulses each of 100 microseconds in duration, with a repetition frequency of a few hundred microseconds, typically set to 400 microseconds.

The unit 3 moreover serves to supply electricity to the light-emitting diodes, with a power that is different from one color to another, in the preferred embodiment of the appliance described here. This power for illuminating the skin during treatment varies from higher to lower on passing from a warmer color to a colder color. It is typically 120 candelas for the red color used in the electroporation step, 56 candelas for the orange color used during the electrophoresis step and 13 candelas for the blue color used during the final step for regenerating the skin.

In accordance with the invention, the appliance described comprises an electronic unit 5 incorporating all the means for controlling the electrical supply means distributing current to the diodes and to the electrode. These control means are available in software form as programs prerecorded in an appropriate circuit board, acting on various parameters to which are assigned different values from one program to another, depending on the conditions prescribed to each program.

The main parameters are principally the overall duration of the treatment cycle, which may typically vary between 20 and 40 minutes, and which is more particularly about 20-25 to 30 minutes, and the respective durations of each of the steps of the cycle, the electroporation sequence especially, in general, having a duration two to three times as long as the durations of the electrophoretic treatment sequence and the chromotherapy regeneration sequence. Another quantity that may likewise be varied is the polarity of the current applied to the treatment electrode, and yet another is the presence or absence of a lithotherapy quartz crystal about which more will be said below.

The designer who prepares the prerecorded programs and the automatic control unit will set the value of the parameters so as to best suit the treatment to, for example, the phototype or skin type of the patient, to the location of the region of skin to be treated and to its state at the time. It will also be possible if required to take into account the nature of the product applied to the skin before the treatment, its form and its composition, by referring to an identification code inscribed on each vial containing one of the lotion formulations to be applied.

By way of example, a suitable program for treating pigmentation marks on light and dry skin, on the forehead or cheeks, would use a treatment cycle of 24 minutes in total length, by applying the pulsed electroporation current under exposure to red light for 15 minutes, then applying the electrophoresis current under exposure to orange light for 5 minutes, before a chromotherapy treatment under blue color for 4 minutes.

The members controlling the switching of the electrical current applied to the electrode act synchronously on the current supplied to the diodes illuminating the skin so as to control the turn-on state of the various diodes in order to change from one color to another. They automatically control the timing of the operating cycle and the timing of the sequences of the appliance by taking account of the value given to the parameters that can be adjusted for each particular application.

A display 6 (FIG. 1), here consisting of a backlit liquid-crystal graphics display, makes it possible to see the choices of the user regarding the treatment conditions that he wishes to apply (phototype, skin type, location, lotion chosen, use of the electrode with a quartz crystal or the electrode without a quartz crystal), and the set points of the treatment program that the appliance defines as a consequence, with values of the parameterizable quantities which will have been set therein automatically. Also shown in FIG. 1 are a circuit breaker 31 and an isolation unit 26 that isolates the circuit supplying the optical elements from the circuit for making the treatment current flow in the electrode 9, this isolation being shown by the dashed line 25.

Before the appliance according to the invention is used, the skin is advantageously coated with appropriate active substances (for example in the form of gels or creams) comprising specific molecules the cosmetic effect of which is optimized by the combined effects of the electrical currents and of the light rays generated by the light-emitting diodes, and by the optional effect of the presence of a mineral element such as a quartz crystal placed on the end of the treatment head.

In the subsequent step, chromotherapy under red color combines its effects with those of electroporation by application of a pulsed current, so as to ensure the pores of the skin are open. Next, during the DC-current electrophoresis step under orange light, certain programs make it possible to increase the magnitude of the current up to a value of about 20 milliamps. The exposure to light prolongs the pore-opening effect of the electroporation step whereas application of the electrophoretic current promotes migration of the active substances present on the skin. Application of the electrophoretic current is in general followed by a final step which uses blue diodes to regenerate the tissues and help to give a lasting effect to the cosmetic treatment carried out.

Figure 2:
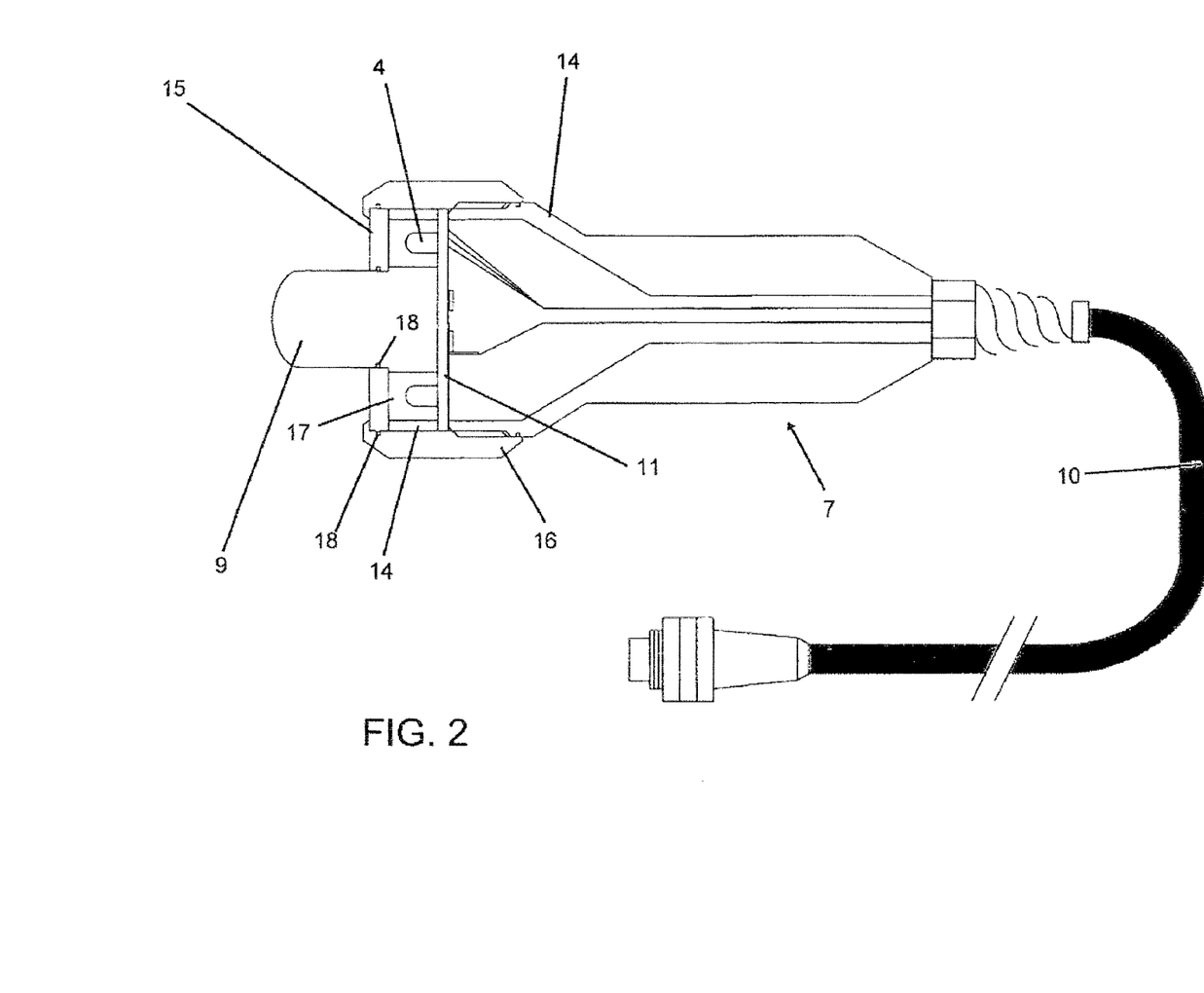
FIG. 2 is a schematic view of a first head of the appliance to be applied to the skin to be treated.

During all these steps, electrical current and light are applied to the skin by means of a treatment head 7 connected to the current generators and means supplying electricity to the diodes via a connector ensuring electrical connection to the housing A at the end of a flexible multiconductor cable 10.

In the treatment head 7, which has a substantially cylindrical general shape, the electrode 9 is placed along the longitudinal axis. Electrically conductive, it consists of an aluminum-based metal alloy. The electrode 9 is mounted in the center of a plate 11, placed through the insulating case 14 of the treatment head. This plate itself consists of an electrical insulator, for example based on epoxy resin. It is on this plate that the light-emitting diodes are also mounted, powered via electrically conductive tracks, supported by the same plate.

As described above, the diodes 4 are arranged alternately by color, so that the illumination delivered is uniformly distributed in a ring around the electrode 9, in immediate proximity to the latter, for each of the colors considered. In the particular case chosen to illustrate as best as possible the invention, the appliance thus comprises three diodes of each of the three colors, distributed at equal angular intervals around the electrode.

According to the embodiment of the appliance illustrated in FIG. 2, the diodes are mounted behind a protective window-pane made of a translucent material 15, which is thus interposed between the diodes 4 and the skin against which the treatment head is placed. The window-pane 15 has substantially the shape of a thin disk, placed around the electrode 9 such that the latter protrudes so as to make good contact with the skin. It essentially has the function of protecting the diodes 4 and the plate 11 during cleaning of the appliance after use. It is therefore important for it to be well sealed so as to isolate the plate 11, which bears electrical connections, and the diodes, from the external environment.

To do this, a ring 16 is threaded around the external periphery of the transparent element 15, and screwed onto the threaded part of the insulating case 14. The ring 16 secures with the case the assembly formed by the plate 11, the diodes 4, the window-pane 15 and the electrode 9, bounding thereby a cavity 17 in which the diodes 4 are housed. A set of O-rings 18 seal the cavity 17 from the surrounding environment.

Figure 3:
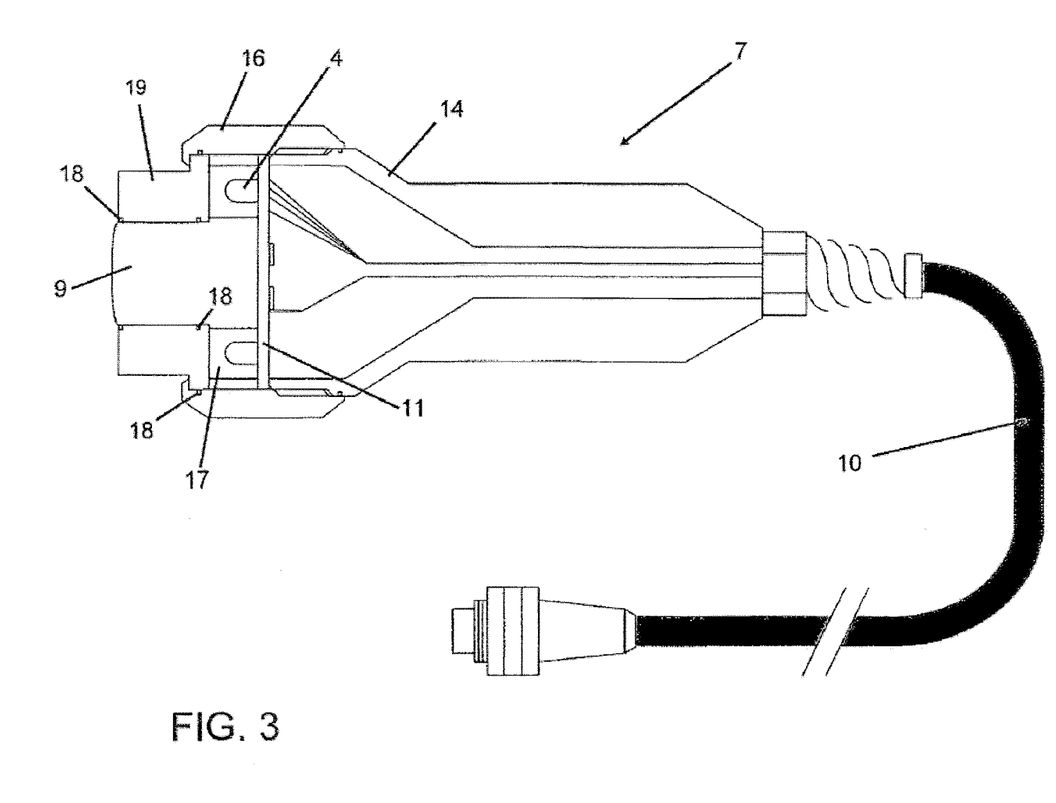
FIG. 3 is a schematic view of another applicator head for the same appliance, interchangeable with the first in its use.

The appliance described comprises a second treatment head, shown in FIG. 3, which is provided so as to be used as a variant to the above head, from which it differs by the presence of a quartz crystal having a lithotherapy effect when it is brought into contact with the skin of the patient.

This quartz crystal 19 replaces the window-pane 15, but in contrast to the latter, it is not set back from the end of the conductive electrode 9. Its presence, combined with that of the color diodes and the current delivered, increases the effect of the cosmetic treatment carried out, by making contact with the skin to be treated at the same time as the electrode 9 is brought into contact with the latter. The quartz crystal 19 is ring-shaped so as to be placed around the electrode 9 advantageously so as to ensure a lithotherapy effect in combination with the electrical electroporation and electrophoresis effects and with the chromotherapy effects of the colored radiation, for an optimal cosmetic treatment action.

It may be seen in the figure that the electrode 9 is shaped so as to protrude slightly relative to the external face of the quartz crystal 19 so as to ensure electrical contact with the skin, while having a flat end so as to allow the mineral element to contact the skin simultaneously.

The applicator head is mounted in a way similar to that illustrated in FIG. 2. However, since the quartz crystal 19 here makes intimate contact with the external surface of the electrode 9 over most of its length, the O-ring 18 intended to seal these two elements is located near the end of the electrode 9 intended to make contact with the skin. This in particular makes it possible to prevent any penetration of traces of active cosmetic substances at the interface between the electrode and the quartz crystal, which substances could contaminate and corrode the electrode. It may also be envisioned, as illustrated in FIG. 3, to doubly seal the interface between the electrode 9 and the quartz crystal 19, by placing an O-ring 18 near each of the faces of the quartz crystal.

Despite its advantages, the quartz-lithotherapy treatment head does not render the quartzless head without its uses. One or the other will be used depending on the accessibility of the region of skin to be treated. Different control programs are associated with each of the two treatment heads. For example, the user will change program at the same time as he passes from an application to the forehead using the quartz head to treatment of the eyelids or around the eyes using the quartzless head.

Other advantages may also become clear to those skilled in the art on reading about the following exemplary implementations, illustrated by the appended figures, which exemplary implementations are given by way of illustration.

EXAMPLE 1

Implementation of the Treatment Appliance Comprising a Head Provided with a Mineral 1) Features of the Appliance Use is made of a treatment appliance that comprised the following:

means (1, 2) for producing an electrical current of preset polarity between an electrode (9) to be applied to the skin and an opposed electrode to be given a reference potential;

illumination means (4) for producing colored light near the electrode;

at the end of an insulating housing to be held in the hand by a practitioner using the appliance, a piece of lithotherapy-effect quartz having a round shape about 4.1 mm in diameter for making contact with the skin situated around the electrode at the same time as the electrode; and an electronic unit programmed to automatically control switching between production of a pulsed electroporation current in a first step of an operating cycle and production of a nonpulsed electrophoresis current in a second step of said cycle, synchronously with the switching of the production of said colored radiation.

The illumination means and the means for producing current are integrated in an applicator head, at the end of an insulating housing.

2) Treating an Individual with the Appliance

A salicylic acid lotion is applied to each cheek and temple on each side of the face, on the skin of an individual's face, the skin being marked by pigmentation marks.

The appliance is then applied to a cheek and a temple on one side of the face, on the surface of which the treatment lotion is placed.

The skin is then subjected, via the appliance, to a first treatment sequence, by applying a pulsed current while simultaneously exposing the skin to red light, for 12 minutes. The frequency of the pulses is 100 µs on-time and 300 µs off-time. The magnitude of the current is 10 mA. The light intensity is 120 candelas.

Next, the skin is subjected, via the appliance, to a second treatment sequence, by applying a DC current while simultaneously exposing the skin to orange light, for about 8 minutes. The magnitude of the current could be varied from 0 to 10 mA. The light intensity is 56 candelas.

The skin is finally subjected to a third treatment sequence, by applying a DC current while simultaneously exposing the skin to blue light, for about 4 minutes. The magnitude of the current is 0 to 10 mA. The light intensity is 13 candelas.

A control is carried out on the same individual, on the side of the face that is not treated with the appliance.

The effects of treatment by means of the cream and the appliance on the one hand, and by means of the cream alone on the other hand, are inspected visually and compared, possibly after each treatment session.

Figure 4:
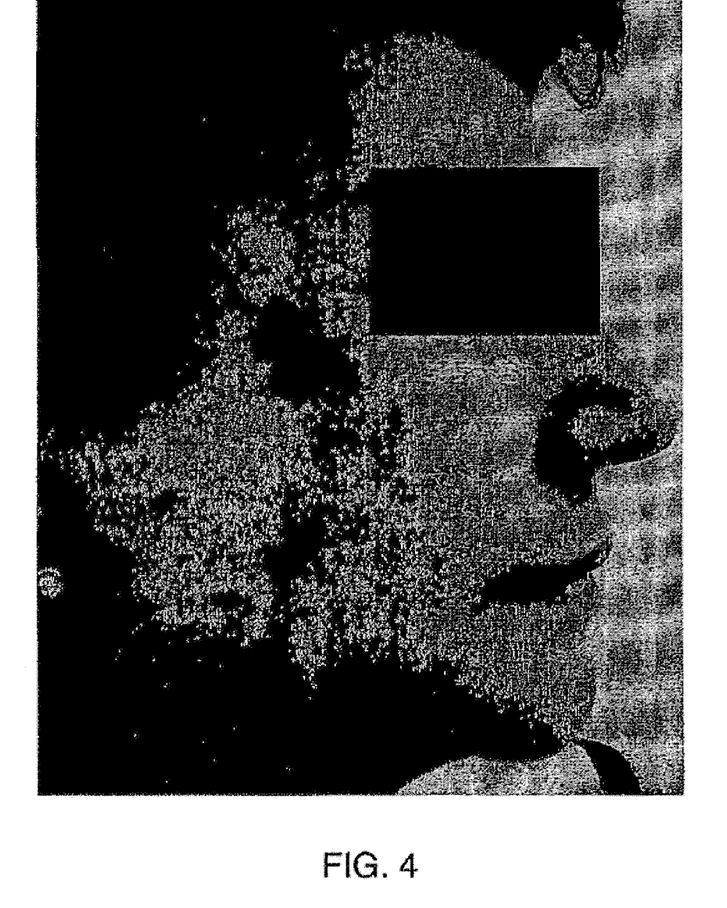
FIG. 4 shows a photograph of the right-hand side of the face of an individual in profile, comprising pigmentation marks on the temples and cheeks, before treatment with the appliance.
Figure 5:
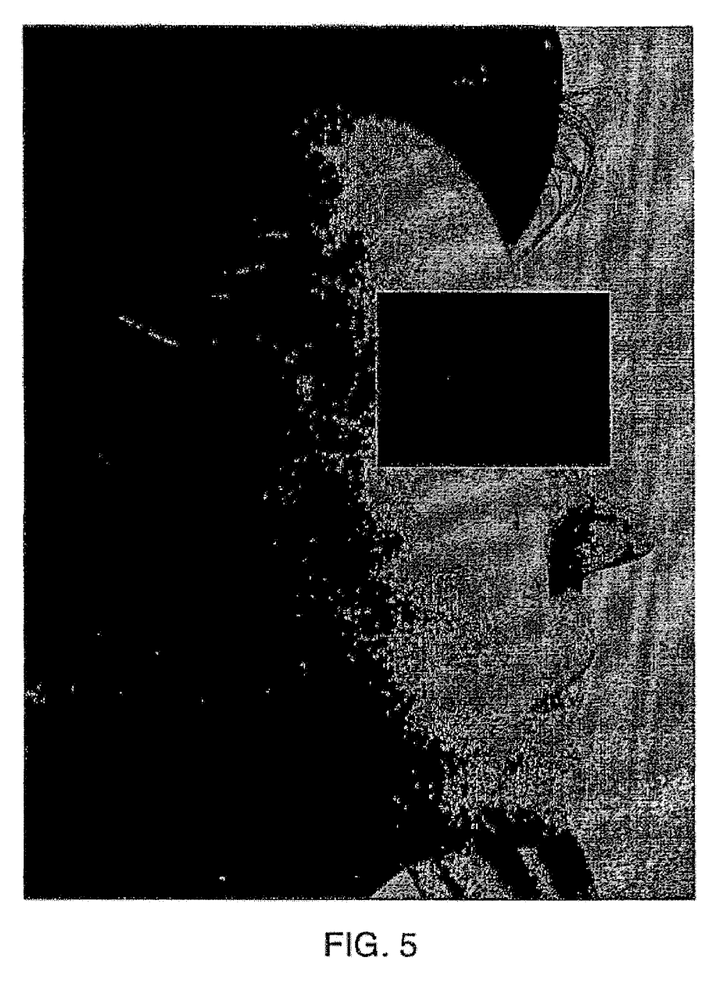
FIG. 5 shows a photograph of the right-hand side of the face of an individual in profile, comprising pigmentation marks on the temples and cheeks, after treatment with the appliance.

Moreover, the side of the face that benefited from treatment with the appliance is inspected visually before application of the appliance (FIG. 4) and after application of the treatment with the appliance (FIG. 5). A reduction in the color (impregnation) of the pigmentation marks of about 20% is observed visually.

EXAMPLE 2

Implementation of the Treatment Appliance for Hard-to-Reach Regions

1) Features of the Appliance

Use is made of a treatment appliance that comprised the following:

means (1, 2) for producing an electrical current of preset polarity between an electrode (9) to be applied to the skin and an opposed electrode to be given a reference potential;

illumination means (4) for producing colored light near the electrode; and an electronic unit programmed to automatically control switching between production of a pulsed electroporation current in a first step of an operating cycle and production of a nonpulsed electrophoresis current in a second step of said cycle, synchronously with the switching of the production of said colored radiation.

The illumination means and the means for producing current are integrated in an applicator head, at the end of an insulating housing.

2) Treating an Individual with the Appliance

A glycolic acid esthetic treatment lotion is applied to each under-eye circle on the skin of an individual's face.

The appliance is then applied to one of the two under-eye circles.

The skin is then subjected, via the appliance, to a first treatment sequence, by applying a pulsed current while simultaneously exposing the skin to red light, for 12 minutes. The frequency of the pulses is 100 μs on-time and 300 μs off-time. The magnitude of the current lay between 0 mA and 10 mA. The light intensity is 120 candelas.

Next, the skin is subjected, via the appliance, to a second treatment sequence, by applying a DC current while simultaneously exposing the skin to orange light, for about 8 minutes. The magnitude of the current is 10 mA. The light intensity is 56 candelas.

The skin is finally subjected to a third treatment sequence, by applying a DC current while simultaneously exposing the skin to blue light, for about 4 minutes. The magnitude of the current is 10 mA. The light intensity is 13 candelas.

A control is carried out on the same individual, on the under-eye circle that is not treated with the appliance.

The effects of treatment by means of the cream and the appliance on the one hand, and by means of the cream alone on the other hand, are inspected visually and compared, possibly after each treatment session.

Figure 6:
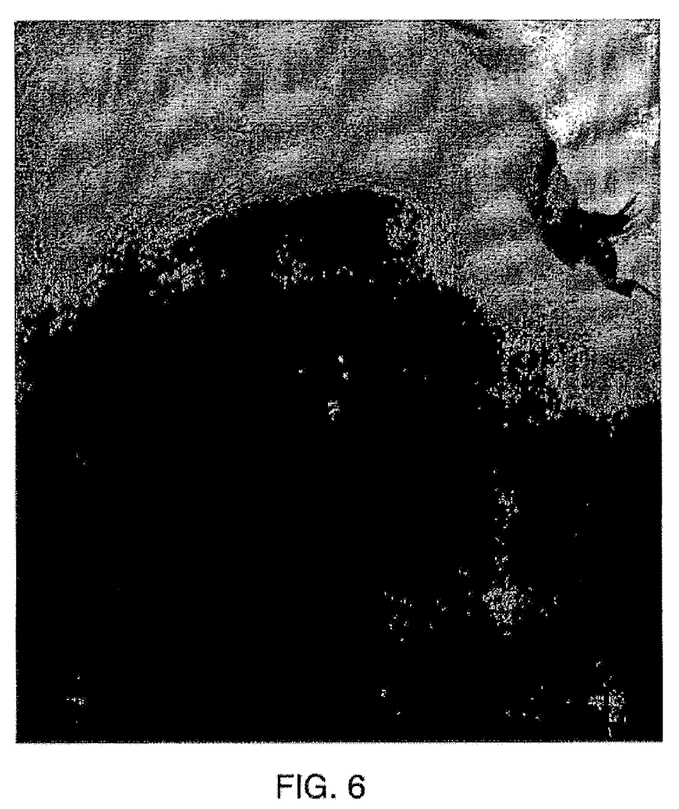
FIG. 6 shows a photograph of the right-hand side of the face of an individual in profile, comprising an under-eye circle noticeable brown-colored, before treatment with the appliance.
Figure 7:
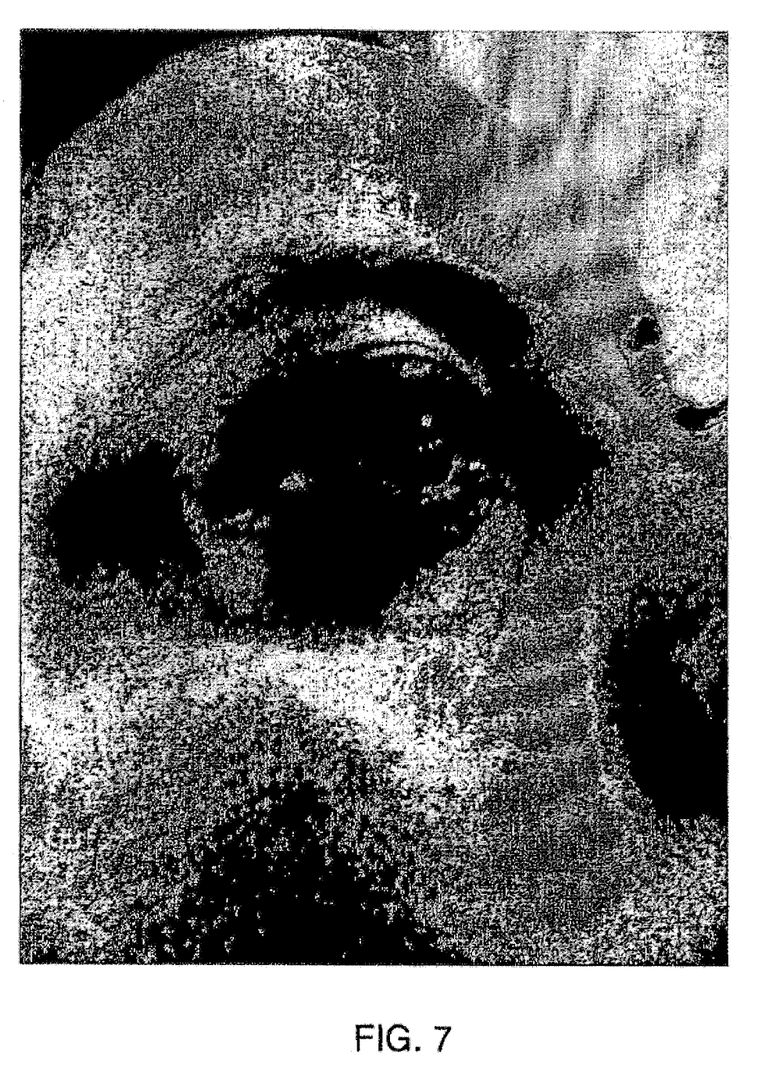
FIG. 7 shows a photograph of the right-hand side of the face of an individual in profile, comprising an under-eye circle, after treatment with the appliance.

Moreover, the under-eye circle that benefited from treatment with the appliance is inspected visually before application of the appliance (FIG. 6) and after application of the treatment with the appliance (FIG. 7). A reduction in the color (impregnation) of the pigmentation marks of about 20% to 30% is observed visually.

The invention claimed is:

1. A method for aesthetic treatment of the skin, in which the skin is subjected to a cycle of successive sequences comprising, in this order, at least a first sequence for treating the skin, called an electroporation sequence, comprising applying a pulsed electroporation current to the skin in combination with simultaneous exposure of the skin under treatment to light having first wavelengths, and a second sequence for treating the skin, called an electrophoresis sequence, comprising applying a DC electrophoresis current in combination with simultaneous exposure of the skin under treatment to light having shorter wavelengths than the first wavelengths.

2. The method as claimed in claim 1, wherein said first electroporation sequence is carried out under exposure to red light and said second electrophoresis sequence is carried out under exposure to orange light.

3. The method as claimed in claim 1, comprising a third sequence for treating the skin, called a regeneration sequence, consisting of a chromotherapy step under exposure to a blue light.

4. The method as claimed in claim 3, in which a current having an electrophoretic action is applied during said sequence for regenerating the skin.

5. The method as claimed in claim 1, wherein, before said cycle of application of a current and simultaneous exposure to colored light, a cosmetic composition is deposited on the skin, in the form of a lotion.

6. An appliance for treating the skin, comprising means for producing an electrical current of predefined polarity, alternately in DC mode and in pulsed mode, between a treatment electrode to be applied to the skin and an opposed electrode to be given a reference potential, means of illumination producing a colored light, alternately of at least two different colors, in the direction of the skin neighboring said treatment electrode, and an electronic unit programmed to automatically control the switching between production of a pulsed electroporation current in a first step of an operating cycle and production of a nonpulsed electrophoresis current in a second step of said cycle, synchronously with switching the production of said colored radiation having first wavelengths to said colored radiation having shorter wavelengths than the first wavelengths.

7. The appliance for treating the skin as claimed in claim 6, in which said electronic unit is furthermore programmed to automatically control the production by said illumination means of a colored radiation for exposing the skin to a blue light, in a third step of said operating cycle, during which a DC electrophoresis current is applied.

8. The appliance for treating the skin as claimed in claim 6, in which said illumination means comprise light-emitting diodes emitting light beams of various colors, which diodes are distributed in a ring behind a protective window-pane placed set back from one end of said treatment electrode to be applied in contact with the skin to be treated, inside an insulating housing to be held in the hand of a practitioner using the appliance.

9. The appliance for treating the skin as claimed in claim 8, in which said diodes emit light of three different colors, respectively in the red, orange and blue, which alternate in succession around said treatment electrode.

10. The appliance for treating the skin as claimed in claim 6, in which said treatment electrode and said illumination means are integrated in an applicator head, at the end of an insulating housing, with a lithotherapy-effect quartz crystal around said treatment electrode that makes contact with the skin at the same time as said electrode.

11. The appliance for treating the skin as claimed in claim 10, comprising two applicator heads to be used interchangeably, one comprising a lithotherapy quartz crystal and the other not comprising this quartz crystal.

12. The appliance as claimed in claim 6, in which said electronic unit comprises prerecorded programs for implementing various standard operating cycles that are differently parameterized, in the respective durations of said steps, the magnitude of the current applied to said treatment electrode being adjustable by the user.

13. A method for treating the skin, in which the skin is subjected to a cycle of successive sequences comprising, in this order, at least a first or electroporation sequence for treating the skin comprising applying a pulsed electroporation current to the skin in combination with simultaneous exposure of the skin under treatment to light having first wavelengths, and a second or electrophoresis sequence for treating the skin, comprising applying a DC electrophoresis current in combination with simultaneous exposure of the skin under treatment to light having shorter wavelengths than the first wavelengths.

14. The method as claimed in claim 2, comprising a third sequence for treating the skin, called a regeneration sequence, consisting of a chromotherapy step under exposure to a blue light.

15. The method as claimed in claim 14, in which a current having an electrophoretic action is applied during said sequence for regenerating the skin.

16. The appliance for treating the skin as claimed in claim 7, in which said illumination means comprise light-emitting diodes emitting light beams of various colors, which diodes are distributed in a ring behind a protective window-pane placed set back from one end of said treatment electrode to be applied in contact with the skin to be treated, inside an insulating housing to be held in the hand of a practitioner using the appliance.

17. The appliance for treating the skin as claimed in claim 16, in which said diodes emit light of three different colors, respectively in the red, orange and blue, which alternate in succession around said treatment electrode.

18. The appliance for treating the skin as claimed in claim 6, wherein first step of said operating cycle is two to three times longer than the second step of said cycle.

\* \* \* \* \*